United States Patent [19]

Guevrekian

[11] Patent Number: 5,715,813
[45] Date of Patent: Feb. 10, 1998

[54] CAPTURE SYSTEM FOR WASTE ANESTHETIC GAS

[76] Inventor: Lawrence Guevrekian, 26 Cedar Pl., Kings Park, N.Y. 11754

[21] Appl. No.: 188,890

[22] Filed: Jan. 31, 1994

[51] Int. Cl.⁶ .................................................. A62B 7/10
[52] U.S. Cl. ........................ 128/205.12; 128/205.19; 128/910
[58] Field of Search ................. 128/203.12, 205.12, 128/205.19, 910

[56] References Cited

U.S. PATENT DOCUMENTS

| | | | |
|---|---|---|---|
| 3,877,691 | 4/1975 | Foster | 128/910 |
| 3,990,112 | 11/1976 | Ciffolillo | 128/910 |
| 4,082,092 | 4/1978 | Foster | 128/910 |
| 4,151,843 | 5/1979 | Brekke et al. | 128/910 |
| 4,219,020 | 8/1980 | Czajka | 128/910 |
| 4,248,218 | 2/1981 | Fischer | 128/910 |
| 4,265,239 | 5/1981 | Fischer, Jr. et al. | 128/910 |
| 4,446,861 | 5/1984 | Tada | 128/910 |
| 4,583,246 | 4/1986 | Griswold | 128/206.22 |
| 4,832,042 | 5/1989 | Poppendiek et al. | 128/205.19 |
| 4,895,172 | 1/1990 | Lindkvist | 128/910 |
| 4,949,714 | 8/1990 | Orr | 128/205.19 |
| 5,033,464 | 7/1991 | Delcastilho | 128/205.19 |
| 5,044,361 | 9/1991 | Werner et al. | 128/203.12 |
| 5,195,512 | 3/1993 | Rosso | 128/205.19 |
| 5,253,641 | 10/1993 | Choate | 128/205.12 |
| 5,345,928 | 9/1994 | Lindkvist | 128/203.12 |

*Primary Examiner*—Aaron J. Lewis
*Attorney, Agent, or Firm*—M. K. Silverman

[57] ABSTRACT

A waste anesthesia capture system includes exhaust apparatus having a rate of fluid flow of at least five times the rate of anesthesia gas delivered to a patient, the exhaust apparatus having a capacity of at least ten cubic feet per minute. The system further includes an exhaust conduit in fluid-integral communication, at a first opening, with the exhaust apparatus. Also included is a Y-shaped anesthesia gas conduct formed of a flexible memory-retaining material. A cross-section of a base portion of that conduit has an output in fluid-integral communication with a second opening of the exhaust conduit, and each of two branches of the Y-shaped conduit define longitudinal axes, the axes having a selectable separation in the range of nine inches to two feet, and each open end of the branches defining a diameter in the range of 0.5 to 4.0 inches.

16 Claims, 4 Drawing Sheets

CAPTURE SYSTEM FOR WASTE ANESTHETIC GAS

BACKGROUND OF THE INVENTION

The present invention relates to a system for the collection and withdrawal of exhaled anesthetic gases from the area about the mouth and nose of a patient. More generally, the instant invention relates to the problem of gas or expired air collection for use in the vicinity of the face or torso of a patient.

Toward the solution of the problem of waste anesthetic gases, considerable attention has been given to the development of anesthetic gas systems that are "closed," that is, to assure that both the inhalation and exhalation of the patient are conducted through a system that is suitably sealed to, thereby, prevent anesthetic gas from contaminating air of the working area. This application assumes that the anesthesia machine is in good working order and free of leaks. The system, however, also clears the area of gases from minor leaks in the anesthesia machine.

It has long since been determined that this problem, if left unaddressed, will bring about harmful side effects to personnel in the work area including possible genetic defects, and will degrade their ability to adequately perform their medical functions. Further, it has been shown that repeated exposure to sub-anesthetic levels of gas can produce harmful long term side effects.

While this problem has been more comprehensively and, generally, satisfactorily, addressed in the context of general medicine, particularly, in the operating room context, the problem has been only superficially considered in the context of dental procedures where the anesthetic gas of choice is nitrous oxide. For example, the operating room professional, when employing an anesthetic, can intubate the patient and ascertain that the exhaled gas is captured, except for cases where the procedure requires the mouth to be open. In such cases, the system could be applied.

A dentist, however, by the nature of his activity, does not enjoy the same luxury. Particularly, a dental patient receiving nitrous oxide may be asked to breathe through his nose. However, frequently, that task becomes difficult because of patient stress, awkwardness of position, foreign objects in the mouth, restricted movement of air through the dental anesthetic mask, and the need for the dentist and his assistants to have continual access to many parts of the patient's mouth. Resultantly, the levels of nitrous oxide found in dental areas often far exceed the recommended safe level therefor.

At present, the state of the art in dental anesthesia arrangements is that of an anesthesia machine that supplies a mixture of nitrous oxide and oxygen at an appropriate rate of 80 ml/min. A nasal mask is attached to the output tubes of the anesthesia machine which tubes supply the anesthetic. Some arrangements employ a vacuum line attached to the mask to scavenge the exhaust gases therefrom. Although this latter technique represents an improvement, the resultant levels of anesthetic gas in the room are nonetheless excessive, that is, in excess of the permissible NIOSH level of exposure of 25 ppm during the period of administration.

It is noted that some manufactures of dental scavenging mask claim to be able to reduce the level of nitrous oxide in a room to below 50 ppm at ideal conditions. However, that is, well above the recommended permissible level of 25 ppm. Such a prior art scavenging mask is represented by U.S. Pat. No. 4,248,218 (1981) to Fischer, entitled Gas Administration Scavenging Mask, and suffers from the limitations, with respect to functionality and a practicality, above set forth.

Other prior art in the gas collection area, known to the inventor, intended for use in the dental context, is U.S. Pat. No. 4,895,172 (1990) to Lindkvist, entitled Gas Collection Device. The system of Lindkvist suffers from numerous shortcomings, which render it unsuitable as a solution to the above set forth problems in the art. More particularly, in Lindkvist the apparatus is physically attached to the patient in an area immediately adjacent to the jaw. Thereby, it is both uncomfortable to the patient and limiting to the dentist with respect to his necessary range of motion relative to the mouth and jaw areas. Further, the fluid flow geometry of Lindkvist is such that it causes a restriction on the performance of the system, that is, complex channels and passageways through which area waste anesthesia gas must pass give rise to turbulence, restrict air movement and increase operating noise of the system. It has been found that turbulence in the channels of gas collection systems is an important factor that restricts the escape of gas. In addition, Lindkvist has not specified the size of the evacuation tubing or the flow rate, both of which are necessary considerations for successful removal of the gases. Also, the quantity of exhaust flow is not addressed.

Further, neither Lindkvist, nor any other art known to the inventor, recognizes the importance of the relationship between the rate of fluid flow of the exhaust means and the rate of anesthetic gas delivery.

For example, the present inventor has determined that a system effective to capture gases escaping from the dental work area must overcome any turbulence within the area. In general, it is therefore necessary to have an exhaust flow rate which is far in excess of the rate of delivery (or loss) of the anesthetic gas. More particularly, the inventor has determined that the exhaust means of a suitably effective system must have a fluid flow rate of at least five times and, preferably, as much as 100 times or more, the rate of inflow of anesthetic gas delivery. Only at such a large differential of flow rates is it possible for the gas collection system to capture the majority of the escaping gas. This relatively high rate of flow is also necessary to overcome air turbulence in the room caused by movement of personnel and placement of equipment and the HVAC system itself. It is noted that HVAC systems frequently incorporate a diffuser to more effectively circulate incoming air to all parts of the room. However, a consequence thereof is additional turbulence which compounds the problem of escape of anesthesia gas.

A further difficulty in Lindkvist and other known art is that no consideration has been given to optimizing the hose having a gas collection interface diameter relative to the various parameters of the area at which the gas of interest is to be collected.

Representative other prior art known to the inventor include U.S. Pat. No. 3,877,691 (1975) to Foster; No. 3,990,119 (1976) to Ciffolillo; No. 4,583,246 (1986) to Griswold; and No. 5,044,361 (1991) to Burkhart.

SUMMARY OF THE INVENTION

The present anesthesia capture system comprises exhaust means having a rate of fluid flow of at least five times the rate of anesthesia gas delivered to a patient, said exhaust means having a capacity of at least ten cubic feet per minute. The system further includes an exhaust conduit in fluid-integral communication, at a first opening thereof, with said exhaust means. Yet further included is a Y-shaped anesthesia gas conduit formed of a flexible memory-retaining material.

A cross-section of a base portion of said conduit has an output in fluid-integral communication with a second opening of said exhaust conduit, and each of two branches of said Y-shaped conduit define longitudinal axes thereof, said axes having a selectable separation therebetween in the range of six inches to two feet, and each open end of said branches defining a diameter in the range of 0.5 to 4.0 inches.

It is accordingly an object of the present invention to provide an improved means of capture of excess anesthetic gases within a dental and/or medical context.

It is another object to provide an improved means of anesthesia gas capture that will afford to the dentist, or physician improved access to work areas in and near the patient's mouth.

It is a further object of the present invention to provide an anesthesia capture system particularly useful in out-patient medical procedures.

It is a yet further object to provide an anesthesia capture system that will reduce exposure of medical personnel to safe levels of gases.

It is a still further object to provide a means of reducing exposure of medical and support personnel to airborne infectious diseases.

The above and yet other objects and advantages of the present invention will become apparent from the hereinafter set forth Brief Description of the Drawings, Detailed Description of the Invention and Claims appended herewith.

DETAILED DESCRIPTION OF THE INVENTION

Figure 1:
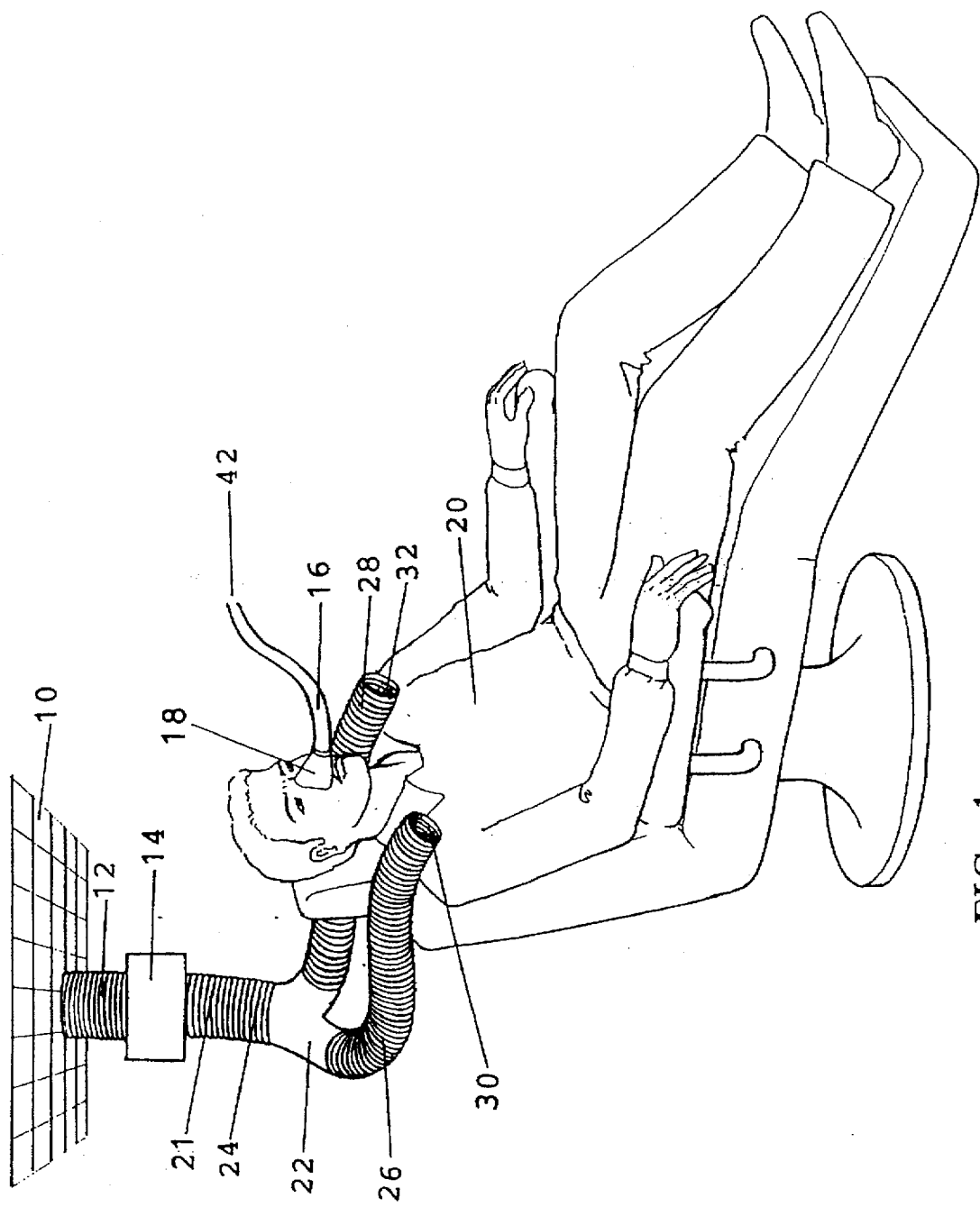
FIG. 1 is a perspective view showing a first application of the inventive anesthesia capture system.

With reference to the perspective view of FIG. 1 there is shown a conventional HVAC exhaust duct 10 to which is provided, in fluid integral communication, an upper exhaust conduit 12 which is operatively connected to said HVAC exhaust duct 10 from exhaust means 14 which is in the nature of an evacuation blower preferably of the sparkless, variable-speed motor type, capable of providing a rate of fluid flow of captured anesthesia gas of at least ten cubic feet per minute and, preferably, of 50 cubic feet or more per minute. This rate of fluid exhaust is about one-third of a typical exhaust rate within said duct 10, and will be in the range of 5 to 30 or more times greater than the rate of delivery of an anesthetic, such as nitrous oxide, from output 16 of an anesthesia machine, providing to the patient a mixture of nitrous oxide and oxygen. Therein nitrous oxide may be in the range of 25 to 80 percent of said mixture.

It is, accordingly, to be appreciated that principles of operation of the instant system depend upon a large differential of flow rates, firstly, between said exhaust means 14 and the anesthetic gas input 16 and, further, between the flow rate of exhaust duct 10 and said exhaust means 14.

As may be noted in the view of FIG. 1, the mixture of nitrous oxide and oxygen is delivered through a nose enveloping mask 18 such that the escape of gas, that is, contamination of the ambient area, can occur through a combination of escape of gas about the periphery of mask 18 and through the sinuses and mouth of patient 20. A relatively high rate of flow is also necessary to overcome air turbulence in the room caused by movement of personnel and placement of equipment as well as the HVAC system itself.

Below exhaust means 14 and above patient 20 is shown lower exhaust conduit 21 (having, for example, a diameter of 3 inches) therebelow, may be seen a hollow Y-shaped gas acquisition conduit 22 which, particularly, includes a base portion 24 which is in fluid-integral communication with said lower exhaust conduit 21. In a given embodiment, conduit 21 may be a completely integral structure with said exhaust conduit 21. Also, exhaust means 14 may be attached directly onto or even partially within HVAC duct 10, thereby obviating the need for conduit 12.

The exhaust means 14 may be placed outside the room, much like a central vacuum cleaning system. This exhaust means may also be common to a number of lower exhaust conduits which service individual rooms. Appropriate means for balancing the air flow from each room should be provided.

As may be further seen in FIG. 1, said Y-shaped gas acquisition conduit 22 further includes branches 26 and 28, each having a definable longitudinal axis, in which inputs 30 and 32 thereto exist at a distance in the range of about 6 inches to about two feet from each other. The material of said Y-shaped conduit 22 is a flexible memory-retaining material such as a polyethylene or related polymer, or flexible aluminum or other such metal which, thereby, may be readily bent to the anatomy of the patient 20 and to a position which is comfortable to the dentist and his assistants.

The diameters of said inputs 30 and 32 of branches 26 and 28 respectively are preferably in the range of 0.5 to 4.0 inches. These inputs 30 and 32 must be increased as a function of an increase in any maximum flow rate to be incorporated.

By virtue of the above structure there is defined a "catch area" around and beneath the mouth of patient 20 from which escaping anesthetic gas will be captured before any further movement from the "catch area."

In terms of the noise factor typically associated with prior art gas capture systems, the noise level of the instant system is reduced as a function of increase in diameter of said inputs 30 and 32. That is, larger diameter hoses, in and about the size of a three-inch diameter, will offer less resistance to flow and thereby reduce the well-known rushing sound of air in such environments. It has been ascertained that through the use of such sized inputs, the sound level of a system in accordance with the instant invention will be less than the sound level of a vacuum aspirator used to evacuate a patient's mouth.

Further, employing the present system, spectrophotometer test results have showed the level of nitrous oxide in a work area to be in the area of five to six ppm throughout the work area. A higher level of 23 ppm was found at anesthesia equipment where a leak existed. Accordingly, even in such a worst case condition, the work environment was found to be below the industry standard safety level of 25 ppm and well below the level of 50 ppm (under optimum conditions) represented as attainable by manufacturers of scavenging masks.

Figure 2:
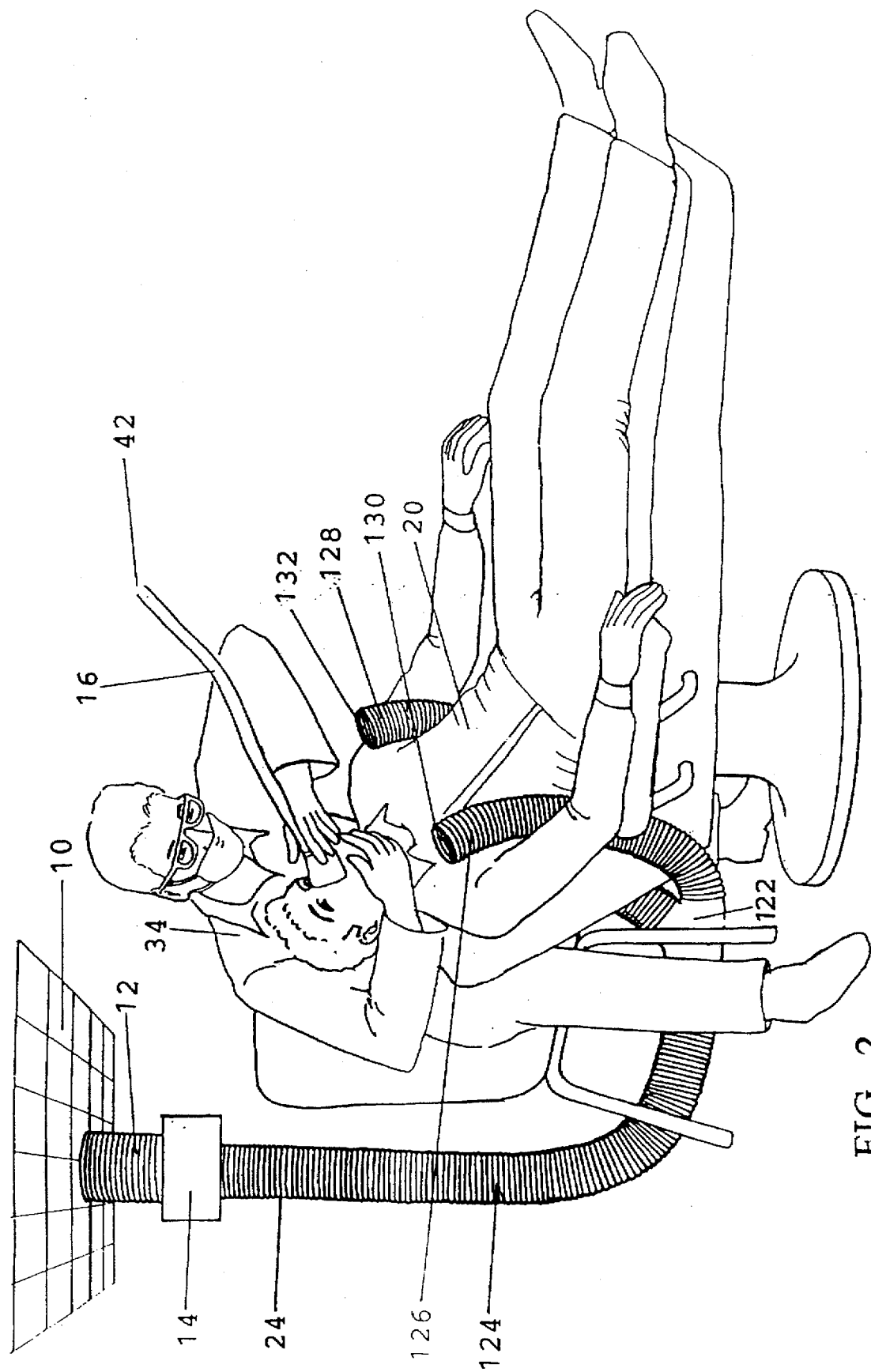
FIG. 2 is a perspective view showing a second application of the inventive system.

With reference to the perspective view of FIG. 2, there is shown a second application of the invention, differing only from the above-described application in the length of the Y-shaped structure 122 and its associated base conduit 124 and delivery branches 126 and 128. The additional length of the conduit segments in this application enable the inputs 130 and 132 to be positioned underneath the armpits of patient 20 thereby enabling anesthesiologist and dentist 34 to work freely in the entire jaw and neck area of the patient without interference from inputs 130 and 132 of the gas acquisition conduit 122. The application of FIG. 2 will, as well, be useful where several dental personnel are required for a given procedure. However, it should be appreciated that, the invention as shown in FIG. 2 may comprise the same equipment in which there are provided hoses 21 and 124 of enhanced length and/or branches 126 and 128 of increased length. Also the conduits employed in the use of FIG. 1 may be readily interchanged with those of the use of FIG. 2.

Figure 3:
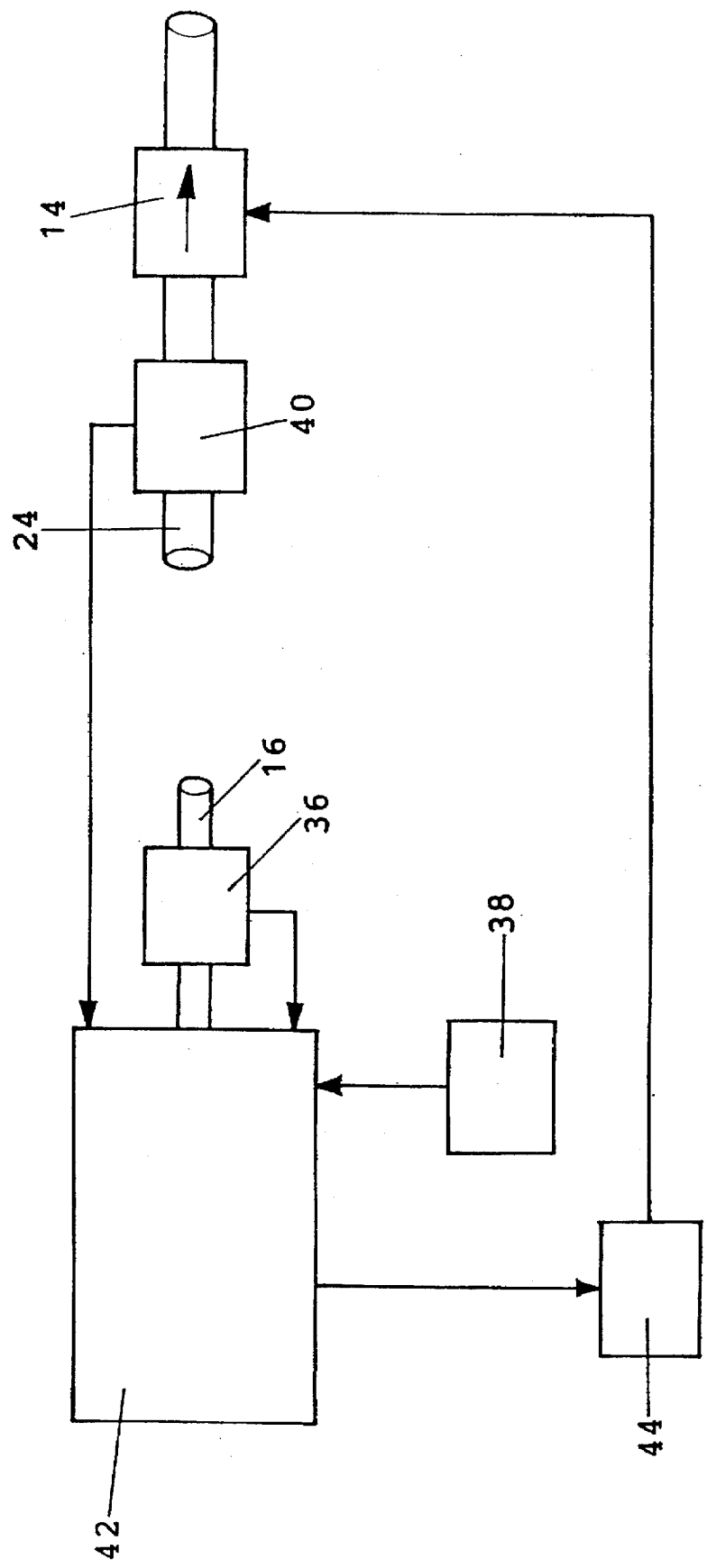
FIG. 3 is an electrical block diagram showing various controls and sensor options of the present system.
Figure 4:
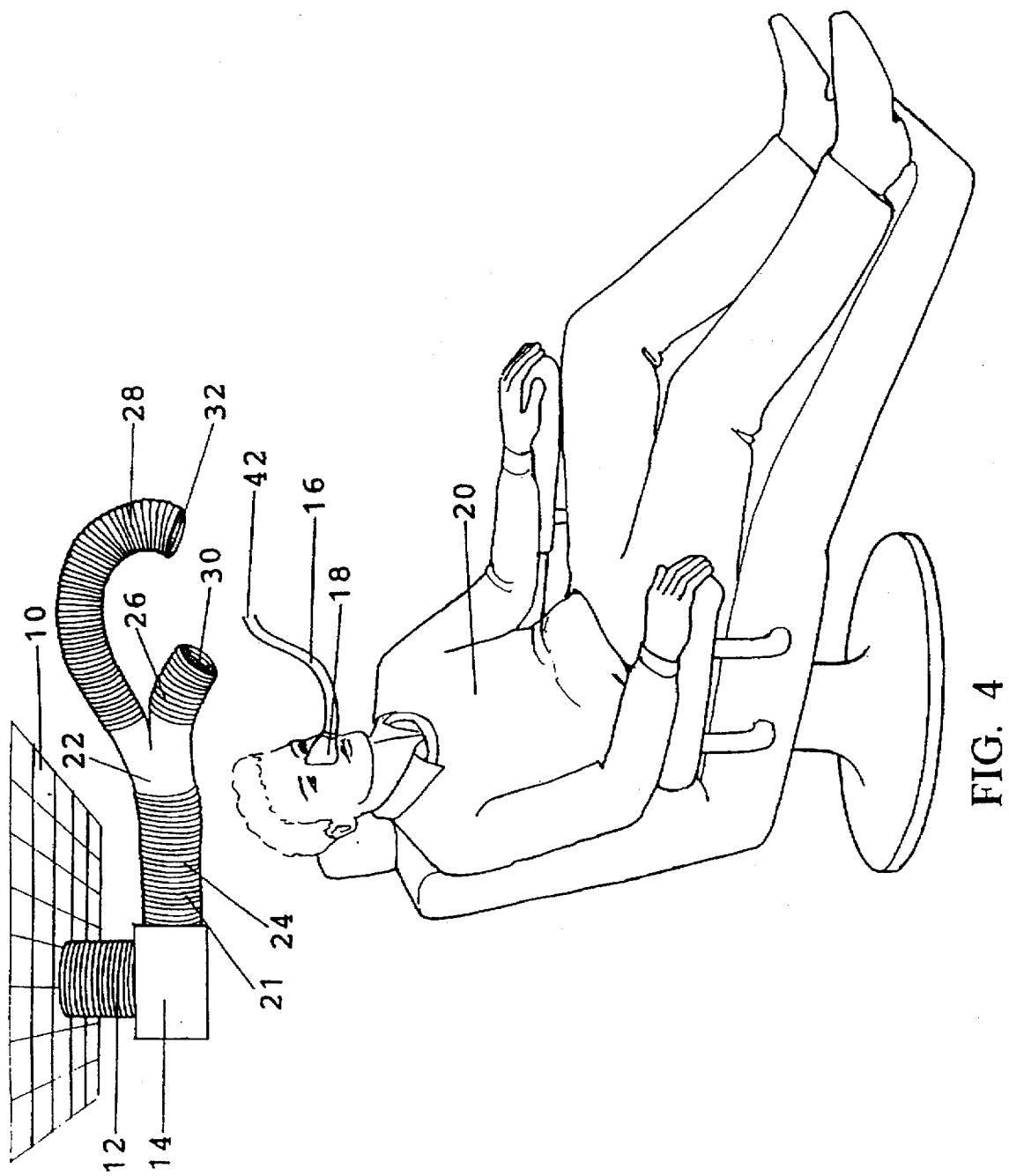
FIG. 4 is a perspective view of a third application of the invention.

With reference to FIG. 3 there is shown a conceptual electrical block diagram view illustration of various sensing and control options that may be integrated into a system in accordance with the present invention. More particularly, therein is shown a sensor 36 for measurement of the quantity of anesthetic gas delivered through input 16, and a sensor 38 for monitoring the concentration of escaped gas from said "catch area." Also there is further employed a flow sensor 40, typically placed within exhaust means 14, the function of which is to advise the operator if the system is not exhausting properly, or, in a given embodiment, to provide an electronic override to or annunciation for the anesthesia machine 42 such that the machine 42 cannot function unless exhaust means 14 is generating a sufficient rate of fluid flow exhaust. There is a minimum flow rate that is set to assure adequate performance under optimum conditions. With continual monitoring of the anesthetic, it would be possible to permit lower flow rates under favorable conditions.

The purpose of sensors 36 and 38 is to provide a variable control means 44 by which the rate of exhaust means 14 may be automatically or, if desired, manually increased as a function of increases of either or both rate of flow of delivered anesthesia gas or concentration of gas contaminants monitored within the work area.

It is also noted that the instant invention contemplates a rate control for the exhaust means 14, operable by dental personnel responsive to other factors that may arise, for example, situations wherein inputs 30 and 32 must be further away from the mouth of the patient or further away from each other, placement of furniture equipment in the room unusual locations, atypical locations of HVAC inlets and returns, and the use of diffusing equipment within the work area. Accordingly, the invention contemplates that the operator will have the means to manually increase rate of exhaust (above a preset minimum) responsive to unusual conditions that may occur in a particular work environment.

It is, further, noted that the present system may be employed even in the absence of HVAC duct 10, by simply interfacing exhaust means 14 with an external area. This is also desirable to reduce the noise of the blower.

It is to be appreciated that, in lieu of he above-described Y-shaped structure, a substantially hood-shaped structure may be employed for the conduit-patient interface.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

Having thus described my invention what I claim as new, useful and non-obvious and, accordingly, secure by Letters Patent of the United States is:

1. An anesthesia gas capture system, comprising:
  (a) exhaust means having a rate of fluid flow of at least five times the rate of flow of an input of anesthesia gas delivery to a patient, said exhaust means having a fluid exhaust capacity of at least 25 cubic feet per minute, said exhaust means further comprising means for actuating said exhaust means responsive to a monitored predetermined level of anesthesia gas contamination within a work area;
  (b) an exhaust conduit in fluid-integral communication, at a first opening thereof, with said exhaust means; and
  (c) a Y-shaped gas acquisition conduit formed of a flexible memory-retaining material, an opening of a base portion of said conduit having an input in fluid integral communication with an appropriate opening of said exhaust conduit, and branches of said Y-shaped conduit defining longitudinal axes having a selectable separation in the range of six inches to two feet, and input ends of said branches defining anesthesia gas acquisition means, each of said input ends having diameters in a range of 0.5 to 4.0 inches.

2. The system as recited in claim 1, in which said exhaust means further comprises:
  means for actuating said exhaust means responsive to actuation of said input of anesthesia gas to a patient.

3. The system as recited in claim 2, further comprising:
  means for varying the rate of flow of said exhaust means responsive to a said rate of flow of anesthesia gas input.

4. The System as recited in claim 2, further comprising:
  means for disabling such input of anesthesia gas into a work area unless said exhaust means is operative.

5. The system as recited in claim 1, further comprising:
  means for varying the rate of flow of said exhaust means responsive to a said rate of flow of anesthesia gas input.

6. The system as recited in claim 5, further comprising:
  means for disabling such input of anesthesia gas into a work area unless said exhaust means is operative.

7. The system as recited in claim 5, further comprising:
  means for varying the rate of flow of said exhaust means responsive to level of monitored anesthesia gas in a work area.

8. The system as recited in claim 7, further comprising:
  means for disabling such input of anesthesia gas into a work area unless said exhaust means is operative.

9. The system as recited in claim 1, further comprising:
  means for varying the rate of flow of said exhaust means responsive to level of monitored anesthesia gas in a work area.

10. The system as recited in claim 9, further comprising:
  means for disabling such input of anesthesia gas into a work area unless said exhaust means is operative.

11. The system as recited in claim 1, further comprising:
  means for disabling such input of anesthesia gas into a work area unless said exhaust means is operative.

12. The system as recited in claim 1, further comprising:
  means for varying the rate of flow of said exhaust means responsive to level of monitored anesthesia gas in a work area.

13. The system as recited in claim 1, further comprising:
  means for disabling such input of anesthesia gas into a work area unless said exhaust means is operative.

14. An anesthesia gas capture system, comprising:

(a) exhaust means having a rate of fluid flow of at least five times the rate of flow of an input of anesthesia gas delivery to a patient, said exhaust means having a fluid exhaust capacity of at least twenty five cubic feet per minute, said exhaust means further comprising means for actuating said exhaust means responsive to a monitored predetermined level of anesthesia gas contamination within a work area;

b) an exhaust conduit in fluid-integral communication, at a first opening thereof, with said exhaust means; and (c) a hood-shaped gas acquisition conduit having an opening as a base portion thereof and having an output in fluid integral communication with an appropriate opening of said exhaust conduit, opposite walls of said acquisition conduit defining a dimension in a range of six inches to two feet, and an input of said opening of said acquisition conduit defining anesthesia gas acquisition means.

15. The system as recited in claim 14, in which said exhaust means further comprises:

means for actuating said exhaust means responsive to actuation of said input of anesthesia gas to a patient.

16. The system as recited in claim 14, further comprising:

means for varying the rate of flow of said exhaust means responsive to a said rate of flow of anesthesia gas input.

* * * * *